United States Patent
Olson et al.

(10) Patent No.: US 9,012,504 B2
(45) Date of Patent: Apr. 21, 2015

(54) NON-ENZYMATIC REMOVAL OF HYDROGEN PEROXIDE FROM PERACIDS

(71) Applicant: Ecolab USA Inc., St. Paul, MN (US)

(72) Inventors: Erik C. Olson, Savage, MN (US); Kim R. Smith, Woodbury, MN (US)

(73) Assignee: Ecolab USA Inc., Saint Paul, MN (US)

( * ) Notice: Subject to any disclaimer, the term of this patent is extended or adjusted under 35 U.S.C. 154(b) by 31 days.

(21) Appl. No.: 13/661,208

(22) Filed: Oct. 26, 2012

(65) Prior Publication Data

US 2014/0121271 A1 May 1, 2014

(51) Int. Cl.
| | | |
|---|---|---|
| *A01N 37/16* | (2006.01) | |
| *A01P 3/00* | (2006.01) | |
| *C09K 3/00* | (2006.01) | |
| *A01P 1/00* | (2006.01) | |
| *A01N 25/22* | (2006.01) | |

(52) U.S. Cl.
CPC ............... *A01N 37/16* (2013.01); *A01N 25/22* (2013.01)

(58) Field of Classification Search
None
See application file for complete search history.

(56) References Cited

U.S. PATENT DOCUMENTS 5,820,841 A * 10/1998 Chen et al. ............... 423/305
6,627,657 B1 * 9/2003 Hilgren et al. ............ 514/553

* cited by examiner

*Primary Examiner* — Robert A Wax
*Assistant Examiner* — Randeep Singh
(74) *Attorney, Agent, or Firm* — McKee, Voorhees & Sease, P.L.C.

(57) ABSTRACT

Peroxycarboxylic acid compositions having reduced hydrogen peroxide content are generated according to the invention, having enhanced antimicrobial efficacy. Simultaneously, a stable hydrogen peroxide and active oxygen coordinating compound complex is generated and has utility as a recycled bleaching component. In particular, methods of using an active oxygen coordinating compound to selectively and non-destructively remove hydrogen peroxide are provided. Preferred active oxygen coordinating compounds suitable for use with the peroxycarboxylic acid compositions include nitrogen-containing compounds, preferably urea, urea copolymers and/or derivatives, PVP, PVP copolymers and/or derivatives, and/or inorganic carbonates.

20 Claims, No Drawings

NON-ENZYMATIC REMOVAL OF HYDROGEN PEROXIDE FROM PERACIDS

FIELD OF THE INVENTION

The invention relates to the non-destructive, non-enzymatic and selective removal of hydrogen peroxide from peroxycarboxylic acid compositions and methods of using the same. In particular, the use of solid urea and other active oxygen coordinating compounds is disclosed herein to reduce the amount of hydrogen peroxide in a peroxycarboxylic acid composition, while providing improved cleaning and antimicrobial efficacy. The active oxygen coordinating compound further provides a stable complex with the hydrogen peroxide suitable for use as an active bleaching source. Active oxygen coordinating compounds suitable for the reduction and/or removal of hydrogen peroxide from peroxycarboxylic acid compositions according to the invention include nitrogen-containing compounds, preferably urea, urea copolymers and/or derivatives, polyvinylpyrrolidone (PVP), PVP copolymers and/or derivatives, and/or inorganic carbonates.

BACKGROUND OF THE INVENTION

Peracid compositions (also referred to as peroxycarboxylic acid compositions) exhibit useful antimicrobial and bleaching activity. Conventional peroxycarboxylic acid compositions typically include short chain peroxycarboxylic acids or mixtures of short chain peroxycarboxylic acids and medium chain peroxycarboxylic acids, such as those disclosed in U.S. Pat. Nos. 5,200,189, 5,314,687, 5,409,713, 5,437,868, 5,489,434, 6,674,538, 6,010,729, 6,111,963, and 6,514,556, each of which is incorporated by reference in its entirety. Such peroxycarboxylic acid compositions usually contain significant quantities of hydrogen peroxide to afford shelf stability of the peracid product. Most often the peroxycarboxylic acid compositions are provided in equilibrium, including for example, peroxyacetic acid, acetic acid, hydrogen peroxide, and water.

Despite the improvements in stability obtained for peroxycarboxylic acid compositions having hydrogen peroxide, the oxidizing agent has detrimental effects on the antimicrobial activity of the peroxycarboxylic acid compositions. Therefore, the reduction of hydrogen peroxide content relative to the peroxycarboxylic acid content of the peracid composition is desired to provide enhancements in antimicrobial efficacy. For example, the use of catalase or enzymatic peroxide destroying agents has been reported to improve antimicrobial and sporicidal efficacy in U.S. Pat. No. 6,627,657, which is incorporated by reference in its entirety. The use of enzymes to selectively but destructively reduce the level of hydrogen peroxide in dilute use solutions of peracetic acid has provided improvements in antimicrobial efficacy of peracid compositions at a point of use. However, improvements to such methods are desired. Further, improvements to such methods that are non-enzymatic, non-destructive and allow the treatment of concentrated peroxycarboxylic acid compositions are desired. Still further, methods that create usable, stable materials from the removed hydrogen peroxide are desired.

Accordingly, it is an objective of the invention to develop non-enzymatic methods for reducing hydrogen peroxide content of peroxycarboxylic acid compositions.

According to a further object of the invention, it is desired develop improved antimicrobial activity peroxycarboxylic acid compositions, namely compositions with improved efficacy against bacterial spores and fungi and other microorganisms with resistance to germicidal materials.

A still further object of the invention is to develop methods of reducing hydrogen peroxide content of peroxycarboxylic acid compositions while simultaneously providing compounds of coordinated urea (or other active oxygen coordinating compound) and hydrogen peroxide for use as bleaching agents.

BRIEF SUMMARY OF THE INVENTION

An advantage of the invention is the improvement of antimicrobial and/or bleaching efficacy as a result of providing reduced hydrogen peroxide content in peroxycarboxylic acid (also referred to herein as a "peracid") compositions. The present invention relates to peracid compositions having significantly improved antimicrobial and/or bleaching efficacy, and methods for generating and employing the enhanced peracid compositions. Typically, the compositions and methods according to the present invention employ one or more suitable active oxygen coordinating compounds to coordinate hydrogen peroxide from the peracid composition.

In an embodiment, the present invention provides a peroxycarboxylic acid composition having reduced hydrogen peroxide concentration comprising from about 0.1-50 wt-% of at least one peroxycarboxylic acid, from about 0.1-50 wt-% of at least one carboxylic acid, and from about 0-8 wt-% hydrogen peroxide. In an aspect, the reduced hydrogen peroxide composition is produced by the process of contacting an aqueous peroxycarboxylic acid composition with a solid active oxygen coordinating compound to reduce and/or eliminate hydrogen peroxide from the composition. In an aspect, the active oxygen coordinating compound is a nitrogen-containing compound that is provided in a weight ratio of the peroxycarboxylic acid to the active oxygen coordinating compound from about 1:1 to about 1:10.

In a further embodiment, the present invention provides a method of reducing hydrogen peroxide from a peroxycarboxylic acid composition comprising providing an aqueous peroxycarboxylic acid composition, contacting the aqueous peroxycarboxylic acid composition with a solid active oxygen coordinating compound to reduce the content of hydrogen peroxide relative to the peroxycarboxylic acid content of the peroxycarboxylic acid composition, and generating a solid complex of the hydrogen peroxide and active oxygen coordinating compound suitable for use as a bleaching agent. In an aspect, the active oxygen coordinating compound is a solid, nitrogen-containing compound. In a further aspect, the ratio of the peroxycarboxylic acid to the active oxygen coordinating compound is from about 1:1 to about 1:10.

In another embodiment, the present invention provides a method of use, namely a method of reducing population of microorganism on an object comprising contacting an object with the reduced hydrogen peroxide peroxycarboxylic acid composition.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION OF THE PREFERRED EMBODIMENT

The present invention relates to antimicrobial and/or bleaching compositions having reduced hydrogen peroxide as a result of treatment with at least one active oxygen coordinating compound, including for example urea, urea copolymers and/or derivatives, PVP, PVP copolymers and/or derivatives. Beneficially, the compositions of the invention having reduced hydrogen peroxide have improved antimicrobial efficacy. In some aspects, an additional benefit of the invention includes an improvement in odor of the peracid composition as a result of the treatment with the active oxygen coordinating compound. In additional aspects, a further benefit is the generation of a stable, solid, reusable urea (or other active oxygen coordinating compound) and hydrogen peroxide complex, which is further suitable for bleaching applications. The compositions can be used on a variety of hard surfaces and methods of employing the same are provided within the scope of the invention.

The embodiments of this invention are not limited to a particular reduced hydrogen peroxide peroxycarboxylic acid composition and methods of generating and employing the same, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form. Numeric ranges recited within the specification are inclusive of the numbers defining the range and include each integer within the defined range.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts.

As used herein, the phrase "air streams" includes food anti-spoilage air circulation systems. Air streams also include air streams typically encountered in hospital, surgical, infirmity, birthing, mortuary, and clinical diagnosis rooms.

The term "alkyl" or "alkyl groups," as used herein, refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups). Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed bacteriocidal and the later, bacteriostatic. A sanitizer and a disinfectant are, by definition, agents which provide antibacterial or bacteriocidal activity. In contrast, a preservative is generally described as an inhibitor or bacteriostatic composition.

For the purpose of this patent application, successful bacteriocidal reduction of microorganisms is achieved when the populations of microorganisms are reduced by about 50%, by significantly more than is achieved by a wash with water, or at least about 0.3-1 $\log_{10}$. Larger reductions in microbial population provide greater levels of protection. In this application, such a population reduction is the minimum acceptable for the processes. Any increased reduction in population of microorganisms is an added benefit that provides higher levels of protection.

The term "disinfectant," as used herein, refers to an agent that kills most vegetative cells including most recognized pathogenic microorganisms, using the procedure described in A.O.A.C. Use Dilution Methods, Official Methods of Analysis of the Association of Official Analytical Chemists, paragraph 955.14 and applicable sections, 15th Edition, 1990 (EPA Guideline 91-2). As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

The phrase "food processing surface" or "food surface," as used herein, refers to a surface of a tool, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, sanitizing gels, cooling towers, food processing antimicrobial garment sprays, and non-to-low-aqueous food preparation lubricants, oils, and rinse additives.

The phrase "health care surface," as used herein, refers to a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.), or woven and non-woven surfaces (such as surgical garments, draperies, bed linens, bandages, etc.), or patient-care equipment (such as respirators, diagnostic equipment, shunts, body scopes, wheel chairs, beds, etc.), or surgical and diagnostic equipment. Health care surfaces include articles and surfaces employed in animal health care.

The term "heterocyclic group," as used herein (e.g. referring to substituted alkyls including a heterocyclic group), includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

The term "instrument," as used herein, refers to the various medical or dental instruments or devices that can benefit from cleaning with a reduced-odor composition according to the present invention. The phrases "medical instrument", "dental instrument", "medical device", "dental device", "medical equipment", or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, arthoscopes and related equipment, and the like, or combinations thereof.

The term "microorganisms," as used herein, refers to any noncellular or unicellular (including colonial) organism. Microorganisms include all prokaryotes. Microorganisms include bacteria (including cyanobacteria), lichens, microfungi, protozoa, virinos, viroids, viruses, and some algae. As used herein, the term "microbe" is synonymous with microorganism.

The phrases "objectionable odor," "offensive odor," or "malodor," as used herein, refer to a sharp, pungent, or acrid odor or atmospheric environment from which a typical person withdraws if they are able to.

The term "object", as used herein, refers to a something material that can be perceived by the senses, directly and/or indirectly. Objects include a surface, including a hard surface (such as glass, ceramics, metal, natural and synthetic rock, wood, and polymeric), an elastomer or plastic, woven and non-woven substrates, a food processing surface, a health care surface, and the like. Objects also include a food product (and its surfaces); a body or stream of water or a gas (e.g., an air stream); and surfaces and articles employed in hospitality and industrial sectors.

The term "sanitizer," as used herein, refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in Germicidal and Detergent Sanitizing Action of Disinfectants, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25° C.+/−2° C., against several test organisms.

The term "sporicide," as used herein, refers to a physical or chemical agent or process having the ability to cause greater than a 90% reduction (1-log order reduction) in the population of spores, such as spores of *Bacillus cereus* or *Bacillus subtilis*, within 30 minutes at ambient temperature. In certain embodiments, the sporicidal compositions of the invention provide greater than a 99% reduction (2-log order reduction), greater than a 99.99% reduction (4-log order reduction), or greater than a 99.999% reduction (5-log order reduction) in such population within at least 30 minutes at ambient temperature.

The term "ware," as used herein, refers to items such as eating and cooking utensils, dishes, and other hard surfaces such as showers, sinks, toilets, bathtubs, countertops, windows, mirrors, transportation vehicles, and floors. As used herein, the term "warewashing" refers to washing, cleaning, or rinsing ware. Ware also refers to items made of plastic. Types of plastics that can be cleaned with the compositions according to the invention include but are not limited to, those that include polycarbonate polymers (PC), acrilonitrile-butadiene-styrene polymers (ABS), and polysulfone polymers (PS). Another exemplary plastic that can be cleaned using the compounds and compositions of the invention include polyethylene terephthalate (PET).

As used herein, the term "waters" includes food process or transport waters. Food process or transport waters include produce transport waters (e.g., as found in flumes, pipe transports, cutters, slicers, blanchers, retort systems, washers, and the like), belt sprays for food transport lines, boot and handwash dip-pans, third-sink rinse waters, and the like. Waters also include domestic and recreational waters such as pools, spas, recreational flumes and water slides, fountains, and the like.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods and compositions of the present invention may comprise, consist essentially of, or consist of the components and ingredients of the present invention as well as other ingredients described herein. As used herein, "consisting essentially of" means that the methods and compositions may include additional steps, components or ingredients, but only if the additional steps, components or ingredients do not materially alter the basic and novel characteristics of the claimed methods and compositions.

Compositions

Peroxycarboxylic acid compositions having reduced hydrogen peroxide concentration are provided according to the present invention. In particular, compositions having reduced concentrations of hydrogen peroxide relative to a peroxycarboxylic acid from conventional equilibrium concentrations are described herein. In addition, hydrogen peroxide and urea (or other active oxygen coordinating compound) complexes are generated from the methods of reducing hydrogen peroxide from a peroxycarboxylic acid composition and can be used for various bleaching applications. Beneficially, the peracids to be treated according to the invention to obtain reduced hydrogen peroxide concentrations include both concentrated and ready-to-use peroxycarboxylic acid compositions. In a preferred aspect, a concentrated peroxycarboxylic acid composition is treated according to the invention to obtain a reduced hydrogen peroxide concentration in the peroxycarboxylic acid composition, preferably having hydrogen peroxide eliminated from the composition.

In an aspect, the peroxycarboxylic acid compositions according to the invention are treated with an active oxygen coordinating compound, including for example being contacted with a urea or other active oxygen coordinating compound in a column (or other substrate) through which the peroxycarboxylic acid composition is passed through to remove hydrogen peroxide from the peroxycarboxylic acid composition. The resultant peroxycarboxylic acid compositions have reduced hydrogen peroxide content, and may further include a surfactant, water, carboxylic acids, other oxidizing agents, chelants, sequestrants, hydrotropes and the like. In an additional aspect, the peroxycarboxylic acid compositions may further include additional functional ingredients as disclosed herein. In an aspect of the invention the treated peroxycarboxylic acid compositions do not include hydrogen peroxide.

While an understanding of the mechanism is not necessary to practice the present invention and while the present invention is not limited to any particular mechanism of action, it is contemplated that, in some embodiments, the peroxycarboxylic acid compositions treated with an active oxygen coordinating compound significantly reduce and/or eliminate hydrogen peroxide from the peroxycarboxylic acid composition. The removal of hydrogen peroxide alters the equilibrium of the peroxycarboxylic acid composition, resulting in increased peroxycarboxylic acid in comparison to the hydrogen peroxide oxidizing agent.

In additional aspects of the invention, the coordination of hydrogen peroxide by the active oxygen coordinating compound forms a complex that is a beneficial source of a bleaching composition, which may be used in addition to the treated peroxycarboxylic acid composition. In additional aspects, the coordination of hydrogen peroxide by the active oxygen coordinating compound further results in a peroxycarboxylic acid composition having improved antimicrobial efficacy.

Active Oxygen Coordinating Compounds

The compositions of the invention are treated with an active oxygen coordinating compound. Active oxygen coordinating compounds may include for example, any non-enzymatic means of reducing hydrogen peroxide from peroxycarboxylic acid compositions. In an aspect, the non-enzymatic reduction of hydrogen peroxide is non-destructive and beneficially results in the coordination of hydrogen peroxide with the active oxygen coordinating compound into a solid raw material suitable for bleaching applications.

In an aspect, the active oxygen coordinating compound is a nitrogen-containing compound, preferably a solid nitrogen-containing compound that selectively forms hydrogen peroxide complexes. In an aspect, the active oxygen coordinating compound is preferably urea, a urea copolymer and/or derivative (such as a urea acid salt), polyvinylpyrrolidone (PVP), a PVP copolymer and/or derivative (such as a PVP acid salt), or an inorganic carbonate. Additional description of PVP derivatives is provided, for example, in U.S. Pat. No. 3,480,557, which is herein incorporated by reference in its entirety, and discloses for example various polymeric N-vinyl heterocyclic compounds.

In a preferred aspect, the active oxygen coordinating compound is a solid source of urea. In a further preferred aspect, the active oxygen coordinating compound is a solid source of PVP. In a further preferred aspect, the active oxygen coordinating compound is a solid inorganic carbonate. In an aspect, the active oxygen coordinating compound is a solid that is provided in a column, cartridge or fluidized bed. For example, the solid active oxygen coordinating compound may be urea that is packed into a column, cartridge or fluidized bed. Further examples of the solid active oxygen coordinating compound may include urea that is incorporated into a filter or bound to a substrate.

An aspect of the invention is the use of the active oxygen coordinating compound material (e.g. urea, PVP, sodium carbonate) unexpectedly preferentially coordinates hydrogen peroxide instead of the peracetic acid (or other applicable peroxycarboxylic or percarboxylic acids) of a peracid composition treated according to the invention.

Each of the suitable substrate forms for the active oxygen coordinating compound may be provided in various physical shapes or sizes. In addition, the substrate forms may be portable and/or removable, so as to enable the use of the active oxygen coordinating compounds at various locations. Further, the substrate forms may also include one or more inlets and one or more outlets while housing or containing the active oxygen coordinating compound. The term "containing" as used herein refers to the substrate form having the active oxygen coordinating compound contained therein. For example, a cartridge may contain the active oxygen coordinating compound in a bound or loss fashion.

In an aspect, the weight ratio of the peroxycarboxylic acid to the active oxygen coordinating compound is from about 1:1 to about 1:10 to provide an adequate reduction of hydrogen peroxide content without significantly reducing the peroxycarboxylic acid content. In a preferred aspect of the invention, the weight ratio of the peroxycarboxylic acid to the active oxygen coordinating compound is from about 1:1 to about 1:4, preferably about 1:1 to about 1:2. Without being limited according to the invention, all ranges recited are inclusive of the numbers defining the range and include each integer within the defined range as well as account for use of either a use concentration and/or a concentrate employed according to the methods of the invention.

As one of skill in the art will ascertain, the weight ratio of the peroxycarboxylic acid to the active oxygen coordinating compound used to achieve the preferred percentage of hydrogen peroxide reduction from the peroxycarboxylic acid composition may vary depending upon the structure of the treated peracid composition, the amount of time for contacting (or treating) the peroxycarboxylic acid composition with the active oxygen coordinating compound.

Peracids

A variety of peroxycarboxylic acids may be employed in the compositions and methods according to the invention. In some embodiments of the invention at least one peroxycarboxylic acid is employed. According to an embodiment of the invention suitable peroxycarboxylic acids include ester peroxycarboxylic acids, alkyl ester peroxycarboxylic acids, sulfoperoxycarboxylic acids, and combinations of several different peroxycarboxylic acids, as described herein. Further description of suitable alkyl ester peroxycarboxylic acids and ester peroxycarboxylic acids according to the invention is included in U.S. Pat. Nos. 7,816,555 and 7,622,606, both entitled "Peroxycarboxylic Acid Compositions with Reduced Odor," hereby expressly incorporated herein in its entirety by reference, including without limitation all drawings and chemical structures contained therein.

The terms "peracid," "peroxyacid," "percarboxylic acid" and "peroxycarboxylic acid" as used herein, refer synonymously to acids having the general formula $R(CO_3H)_n$. The R group can be saturated or unsaturated as well as substituted or unsubstituted. As described herein, R is an alkyl, arylalkyl, cycloalkyl, aromatic, heterocyclic, or ester group, such as an alkyl ester group. N is one, two, or three, and named by prefixing the parent acid with peroxy. Ester groups are defined as R groups including organic moieties (such as those listed above for R) and ester moieties. Exemplary ester groups include aliphatic ester groups, such as $R_1OC(O)R_2$, where each of $R_1$ and $R_2$ can be aliphatic, preferably alkyl, groups described above for R. Preferably $R_1$ and $R_2$ are each independently small alkyl groups, such as alkyl groups with 1 to 5 carbon atoms. As one skilled in the art shall appreciate, peroxycarboxylic acids are not as stable as carboxylic acids, their stability generally increases with increasing molecular weight. Thermal decomposition of these acids can generally proceed by free radical and nonradical paths, by photodecomposition or radical-induced decomposition, or by the action of metal ions or complexes. Percarboxylic acids can be made by the direct, acid catalyzed equilibrium action of hydrogen peroxide with the carboxylic acid, by autoxidation of aldehydes, or from acid chlorides, and hydrides, or carboxylic anhydrides with hydrogen or sodium peroxide.

Exemplary peroxycarboxylic acids useful in the compositions of the present invention include peroxyformic, peroxyacetic, peroxypropionic, peroxybutanoic, peroxypentanoic, peroxyhexanoic, peroxyheptanoic, peroxyoctanoic, peroxynonanoic, peroxydecanoic, peroxyundecanoic, peroxydodecanoic, peroxylactic, peroxycitric, peroxymaleic, peroxyascorbic, peroxyhydroxyacetic (peroxyglycolic), peroxyoxalic, peroxymalonic, peroxysuccinic, peroxyglutaric, peroxyadipic, peroxypimelic, peroxysuberic, and peroxysebacic acid, and mixtures thereof. Useful peroxycarboxylic acids also include the ester peroxycarboxylic acids described herein and compositions of the present invention including those ester peroxycarboxylic acids. Peroxy forms of carboxylic acids with more than one carboxylate moiety can have one or more of the carboxyl moieties present as peroxycarboxyl moieties. These peroxycarboxylic acids have been found to provide good antimicrobial action with good stability in aqueous mixtures. In a preferred embodiment, the composition of the invention utilizes a combination of several different peroxycarboxylic acids.

In an embodiment, the compositions of the invention utilize a combination of several different peroxycarboxylic acids, including mixed peracid compositions. The terms "mixed" or "mixture" when used relating to "peracid composition," "peroxycarboxylic acid composition," "peracids" or "peroxycarboxylic acids" refer to a composition or mixture including more than one peracid, such as a peroxycarboxylic acid, such as a composition or mixture including peroxyacetic acid and peroxyoctanoic acid.

According to one embodiment, the composition includes one or more small $C_2$-$C_4$ peroxycarboxylic acids, one or more large $C_8$-$C_{12}$ peroxycarboxylic acids, one or more ester peroxycarboxylic acids, one or more alkyl ester peroxycarboxylic acids, and/or one or more mono- or di-peroxycarboxylic acid having up to 12 carbon atoms. According to a further embodiment, the peroxycarboxylic acid has from 2 to 12 carbon atoms. According to an embodiment, the peroxycarboxylic acids include peroxyacetic acid (POAA) (or peracetic acid having the formula $CH_3COOOH$) and/or peroxyoctanoic acid (POOA) (or peroctanoic acid having the formula, for example, of n-peroxyoctanoic acid: $CH_3(CH_2)_6COOOH$).

According to an additional embodiment of the invention one or more sulfoperoxycarboxylic acid may also be used in the compositions disclosed herein. As used herein, the term "sulfoperoxycarboxylic acid," "sulfonated peracid," or "sulfonated peroxycarboxylic acid" refers to the peroxycarboxylic acid form of a sulfonated carboxylic acid. In some embodiments, the sulfonated peracids of the present invention are mid-chain sulfonated peracids. As used herein, the term "mid-chain sulfonated peracid" refers to a peracid compound that includes a sulfonate group attached to a carbon that is at least one carbon (e.g., the three position or further) from the carbon of the percarboxylic acid group in the carbon backbone of the percarboxylic acid chain, wherein the at least one carbon is not in the terminal position. As used herein, the term "terminal position," refers to the carbon on the carbon backbone chain of a percarboxylic acid that is furthest from the percarboxyl group.

According to an embodiment of the invention, sulfoperoxycarboxylic acids have the following general formula:

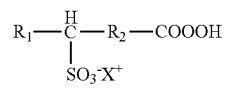

wherein $R_1$ is hydrogen, or a substituted or unsubstituted alkyl group; $R_2$ is a substituted or unsubstituted alkyl group; X is hydrogen, a cationic group, or an ester forming moiety; or salts or esters thereof.

In some embodiments, $R_1$ is a substituted or unsubstituted $C_m$ alkyl group; X is hydrogen a cationic group, or an ester forming moiety; $R_2$ is a substituted or unsubstituted $C_n$ alkyl group; m=1 to 10; n=1 to 10; and m+n is less than 18, or salts, esters or mixtures thereof. In some embodiments, $R_1$ is hydrogen. In other embodiments, $R_1$ is a substituted or unsubstituted alkyl group. In some embodiments, $R_1$ is a substituted or unsubstituted alkyl group that does not include a cyclic alkyl group. In some embodiments, $R_1$ is a substituted alkyl group. In some embodiments, $R_1$ is an unsubstituted $C_1$-$C_9$ alkyl group. In some embodiments, $R_1$ is an unsubstituted $C_7$ or $C_9$ alkyl. In other embodiments, $R_1$ is a substituted $C_8$-$C_{10}$ alkyl group. In some embodiments, $R_1$ is a substituted $C_8$-$C_{10}$ alkyl group is substituted with at least 1, or at least 2 hydroxyl groups. In still yet other embodiments, $R_1$ is a substituted $C_1$-$C_9$ alkyl group. In some embodiments, $R_1$ is a substituted $C_1$-$C_9$ substituted alkyl group is substituted with at least 1 $SO_3H$ group. In other embodiments, $R_1$ is a $C_9$-$C_{10}$ substituted alkyl group. In some embodiments, $R_1$ is a substituted $C_9$-$C_{10}$ alkyl group wherein at least two of the carbons on the carbon backbone form a heterocyclic group. In some embodiments, the heterocyclic group is an epoxide group.

In further embodiments, $R_2$ is a substituted $C_1$-$C_{10}$ alkyl group. In some embodiments, $R_2$ is a substituted $C_8$-$C_{10}$ alkyl. In some embodiments, $R_2$ is an unsubstituted $C_6$-$C_9$ alkyl. In other embodiments, $R_2$ is a $C_8$-$C_{10}$ alkyl group substituted with at least one hydroxyl group. In some embodiments, $R_2$ is a $C_{10}$ alkyl group substituted with at least two hydroxyl groups. In other embodiments, $R_2$ is a $C_8$ alkyl group substituted with at least one $SO_3H$ group. In some embodiments, $R_2$ is a substituted $C_9$ group, wherein at least two of the carbons on the carbon backbone form a heterocyclic group. In some embodiments, the heterocyclic group is an epoxide group. In some embodiments, $R_1$ is a $C_8$-$C_9$ substituted or unsubstituted alkyl, and $R_2$ is a $C_7$-$C_8$ substituted or unsubstituted alkyl.

Further description of suitable sulfoperoxycarboxylic acids, and methods of making the same, according to the invention are included in U.S. patent application Ser. Nos. 12/568,493 and 12/413,189, entitled "Sulfoperoxycarboxylic Acids, Their Preparation and Methods of Use as Bleaching and Antimicrobial Agents," hereby expressly incorporated herein in its entirety by reference, including without limitation all drawings and chemical structures contained therein.

According to an additional embodiment of the invention one or more carboxylic acids may also be used in the compositions disclosed herein. Generally, carboxylic acids have the formula R—COOH wherein the R can represent any number of different groups including aliphatic groups, alicyclic groups, aromatic groups, heterocyclic groups, and ester groups, such as alkyl ester groups, all of which can be saturated or unsaturated and/or substituted or unsubstituted. Carboxylic acids can have one, two, three, or more carboxyl groups. Preferred ester groups include aliphatic ester groups, such as $R_1OC(O)R_2$— where each of $R_1$ and $R_2$ can be aliphatic, preferably alkyl, groups described above for R. Preferably $R_1$ and $R_2$ are each independently small alkyl groups, such as alkyl groups with 1 to 4 carbon atoms.

The composition of the invention can employ carboxylic acids containing as many as 22 carbon atoms. Examples of suitable carboxylic acids include formic, acetic, propionic, butanoic, pentanoic, hexanoic, heptanoic, octanoic, nonanoic, decanoic, undecanoic, dodecanoic, lactic, maleic, ascorbic, citric, hydroxyacetic (glycolic), neopentanoic, neoheptanoic, neodecanoic, oxalic, malonic, succinic, glutaric, adipic, pimelic suberic, and sebacic acid. Examples of suitable alkyl ester carboxylic acids include monomethyl oxalic acid, monomethyl malonic acid, monomethyl succinic acid, monomethyl glutaric acid, monomethyl adipic acid, monomethyl pimelic acid, monomethyl suberic acid, and monomethyl sebacic acid; monoethyl oxalic acid, monoethyl malonic acid, monoethyl succinic acid, monoethyl glutaric acid, monoethyl adipic acid, monoethyl pimelic acid, monoethyl suberic acid, and monoethyl sebacic acid; monopropyl oxalic acid, monopropyl malonic acid, monopropyl succinic acid, monopropyl glutaric acid, monopropyl adipic acid, monopropyl pimelic acid, monopropyl suberic acid, and monopropyl sebacic acid, in which propyl can be n- or isopropyl; and monobutyl oxalic acid, monobutyl malonic acid, monobutyl succinic acid, monobutyl glutaric acid, monobutyl adipic acid, monobutyl pimelic acid, monobutyl suberic acid, and monobutyl sebacic acid, in which butyl can be n-, iso-, or t-butyl.

In some embodiments, the carboxylic acid for use with the compositions of the present invention is a $C_2$ to $C_{12}$ carboxylic acid. In some embodiments, the carboxylic acid for use with the compositions of the present invention is a $C_5$ to $C_{11}$ carboxylic acid. In some embodiments, the carboxylic acid for use with the compositions of the present invention is a $C_1$ to $C_4$ carboxylic acid. Examples of suitable carboxylic acids include, but are not limited to, formic, acetic, propionic, butanoic, pentanoic, hexanoic, heptanoic, octanoic, nonanoic, decanoic, undecanoic, dodecanoic, as well as their branched isomers, lactic, maleic, ascorbic, citric, hydroxyacetic, neopentanoic, neoheptanoic, neodecanoic, oxalic, malonic, succinic, glutaric, adipic, pimelic subric acid, and mixtures thereof. Carboxylic acids that are generally useful include ester carboxylic acids, such as alkyl ester carboxylic acids.

In some embodiments, the compositions of the present invention include a combination of peroxycarboxylic acids and carboxylic acids. According to an embodiment, the compositions of the present invention include at least one sulfoperoxycarboxylic acid and at least one carboxylic and/or percarboxylic acid. In some embodiments, the compositions of the present invention include at least two, at least three, or at least four or more carboxylic and/or peroxycarboxylic acids.

The chemical structures herein, including the peroxycarboxylic acids, are drawn according to the conventional standards known in the art. Thus, where an atom, such as a carbon atom, as drawn appears to have an unsatisfied valency, then that valency is assumed to be satisfied by a hydrogen atom, even though that hydrogen atom is not necessarily explicitly drawn. The structures of some of the compounds of this invention include stereogenic carbon atoms. It is to be understood that isomers arising from such asymmetry (e.g., all enantiomers and diastereomers) are included within the scope of this invention unless indicated otherwise. That is, unless otherwise stipulated, any chiral carbon center may be of either (R)- or (S)-stereochemistry. Such isomers can be obtained in substantially pure form by classical separation techniques and by stereochemically-controlled synthesis. Furthermore, alkenes can include either the E- or Z-geometry, where appropriate. In addition, the compounds of the present invention may exist in unsolvated as well as solvated forms with acceptable solvents such as water, THF, ethanol, and the like. In general, the solvated forms are considered equivalent to the unsolvated forms for the purposes of the present invention.

In a preferred embodiment, the peroxycarboxylic acids, carboxylic acids and/or sulfoperoxycarboxylic acid are provided in an aqueous solution. In a further preferred embodiment, the peroxycarboxylic acids, carboxylic acids and/or sulfoperoxycarboxylic acids are provided in a concentrated or use aqueous solution. In a preferred aspect, the peroxycarboxylic acids, carboxylic acids and/or sulfoperoxycarboxylic acids are not solid compositions due to their application of use according to the methods of the invention disclosed herein.

Without being limited by a particular method of generating or providing a peroxycarboxylic acid composition, in most aspects according to the invention, an acid-catalyzed equilibrium reaction is employed to provide a peroxycarboxylic acid, hydrogen peroxide, and a corresponding carboxylic acid. The components will move toward equilibrium in relative proportions of each constituent and concentrations of the carboxylic acid and the hydrogen peroxide used as starting materials. As the mixture approaches equilibrium, the proportion of peroxycarboxylic acid increases until a maximum is obtained at equilibrium. The rate at which the composition moves toward equilibrium can depend on the concentrations of the reactants, the prevailing temperature, and/or a concentration of a catalyst such as, for example, a strong organic or inorganic acid (e.g., phosphoric acid, phosphonic acid, sulfuric acid, sulfonic acid, etc.). The compositions and methods of the invention provide an improved means of maximizing the concentration of peroxycarboxylic acid and minimizing the concentration of hydrogen peroxide relative to each other.

Oxidizing Agents

When present in the peroxycarboxylic acid compositions according to the invention, any of a variety of oxidizing agents may be employed, for example, hydrogen peroxide. Initially, the oxidizing agent can be present in a peroxycarboxylic acid composition at an amount effective to convert a fatty acid, such as a carboxylic acid or a sulfonated carboxylic acid to a peroxycarboxylic acid or a sulfonated peroxycarboxylic acid. In some embodiments, the oxidizing agent can also have antimicrobial activity. In other embodiments, the oxidizing agent is present in an amount insufficient to exhibit antimicrobial activity.

Examples of inorganic oxidizing agents include the following types of compounds or sources of these compounds, or alkali metal salts including these types of compounds, or forming an adduct therewith: hydrogen peroxide, urea-hydrogen peroxide complexes or hydrogen peroxide donors of: group 1 (IA) oxidizing agents, for example lithium peroxide, sodium peroxide; group 2 (IIA) oxidizing agents, for example magnesium peroxide, calcium peroxide, strontium peroxide, barium peroxide; group 12 (IIB) oxidizing agents, for example zinc peroxide; group 13 (IIIA) oxidizing agents, for example boron compounds, such as perborates, for example sodium perborate hexahydrate of the formula $Na_2[B_2(O_2)_2(OH)_4]6H_2O$ (also called sodium perborate tetrahydrate); sodium peroxyborate tetrahydrate of the formula $Na_2B_2(O_2)_2[(OH)_4]4H_2O$ (also called sodium perborate trihydrate); sodium peroxyborate of the formula $Na_2[B_2(O_2)_2(OH)_{-4}]$ (also called sodium perborate monohydrate); group 14 (IVA) oxidizing agents, for example persilicates and peroxycarbonates, which are also called percarbonates, such as persilicates or peroxycarbonates of alkali metals; group 15 (VA) oxidizing agents, for example peroxynitrous acid and its salts; peroxyphosphoric acids and their salts, for example, perphosphates; group 16 (VIA) oxidizing agents, for example peroxysulfuric acids and their salts, such as peroxymonosulfuric and peroxydisulfuric acids, and their salts, such as persulfates, for example, sodium persulfate; and group VIIa oxidizing agents such as sodium periodate, potassium perchlorate. Other active inorganic oxygen compounds can include transition metal peroxides; and other such peroxygen compounds, and mixtures thereof.

In some embodiments, the compositions of the present invention employ one or more of the inorganic oxidizing agents listed above. Suitable inorganic oxidizing agents include ozone, hydrogen peroxide, hydrogen peroxide adduct, group IIIA oxidizing agent, or hydrogen peroxide donors of group VIA oxidizing agent, group VA oxidizing agent, group VIIA oxidizing agent, or mixtures thereof. Suitable examples of such inorganic oxidizing agents include percarbonate, perborate, persulfate, perphosphate, persilicate, or mixtures thereof.

In some aspects of the invention, the peroxycarboxylic acid compositions have significantly reduced content of the oxidizing agent, namely hydrogen peroxide. In preferred aspects of the invention, the peroxycarboxylic acid compositions have essentially no oxidizing agent, namely hydrogen peroxide, as a result of the methods of treatment disclosed herein.

In some aspects, the treated peroxycarboxylic acid composition has at least about 20 wt-%, at least about 25 wt-%, at least about 30 wt-%, at least about 35 wt-%, at least about 40 wt-%, at least about 45 wt-%, at least about 50 wt-%, at least about 55 wt-%, at least about 60 wt-%, or at least about 65 wt-%, or at least about 70 wt-% hydrogen peroxide removed from the composition. In more preferred aspects, the peroxycarboxylic acid composition has at least about 75 wt-% hydrogen peroxide removed from the composition, preferably at least about 80 wt-% hydrogen peroxide removed from the composition, preferably remove at least about 85 wt-% hydrogen peroxide removed from the composition, preferably remove at least about 90% hydrogen peroxide removed from the composition, preferably remove at least about 95 wt-% hydrogen peroxide removed from the composition, and still more preferably about 100 wt-% hydrogen peroxide removed from the composition. Without being limited according to the invention, all ranges recited are inclusive of the numbers defining the range and include each integer within the defined range.

In some aspects, the treated peroxycarboxylic acid composition has from about 0 wt-% to about 15 wt-% oxidizing agent, such as hydrogen peroxide, in the composition, preferably from about 0 wt-% to about 10 wt-% hydrogen peroxide, more preferably from about 0 wt-% to about 8 wt-% hydrogen peroxide, and still more preferably from about 0 wt-% to about 5 wt-% hydrogen peroxide. Without being limited according to the invention, all ranges recited are inclusive of the numbers defining the range and include each integer within the defined range.

In some aspects, the ratio of peroxycarboxylic acid to hydrogen peroxide is greater than 1:1, preferably greater than 2:1, preferably greater than 3:1, preferably greater than 4:1, preferably greater than 5:1. The ratios are expressed in parts by weight of peroxycarboxylic acid to each part by weight of hydrogen peroxide. Without being limited according to the invention, all ranges recited are inclusive of the numbers defining the range and include each integer within the defined range.

Surfactants

In some aspects of the invention, the peroxycarboxylic acid compositions may include at least one surfactant. Surfactants may be included in the compositions to enhance microbial efficacy, increase solubility of the peroxycarboxylic acid and/or to maintain the pH of the composition. According to an embodiment of the invention, a surfactant may include a hydrotrope coupler or solubilizer, which can be used to ensure that the composition remains phase stable.

Surfactants suitable for use with the compositions of the present invention are disclosed for example in Kirk-Othmer, Encyclopedia of Chemical Technology, Third Edition, volume 8, pages 900-912, which is herein incorporated by reference in its entirety. Particularly suitable surfactants for use according to embodiments of the invention include, for example, nonionic, anionic, amphoteric, and/or cationic surfactants.

Nonionic Surfactants

Suitable nonionic surfactants suitable for use with the compositions of the present invention include alkoxylated surfactants. Suitable alkoxylated surfactants include EO/PO copolymers, capped EO/PO copolymers, alcohol alkoxylates, capped alcohol alkoxylates, mixtures thereof, or the like. Suitable alkoxylated surfactants for use as solvents include EO/PO block copolymers, such as the Pluronic and reverse Pluronic surfactants; alcohol alkoxylates, such as Dehypon LS-54 (R-(EO)$_5$(PO)$_4$) and Dehypon LS-36 (R-(EO)$_3$(PO)$_6$); and capped alcohol alkoxylates, such as Plurafac LF221 and Tegoten EC11; mixtures thereof, or the like.

Semi-Polar Nonionic Surfactants

The semi-polar type of nonionic surface active agents are another class of nonionic surfactant useful in compositions of the present invention. Semi-polar nonionic surfactants include the amine oxides, phosphine oxides, sulfoxides and their alkoxylated derivatives. Amine oxides are tertiary amine oxides corresponding to the general formula:

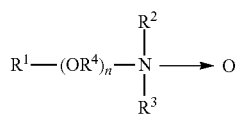

wherein the arrow is a conventional representation of a semi-polar bond; and, $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 24 carbon atoms; $R^2$ and $R^3$ are alkyl or hydroxyalkyl of 1-3 carbon atoms or a mixture thereof; $R^2$ and $R^3$ can be attached to each other, e.g. through an oxygen or nitrogen atom, to form a ring structure; $R^4$ is an alkylene or a hydroxyalkylene group containing 2 to 3 carbon atoms; and n ranges from 0 to about 20. An amine oxide can be generated from the corresponding amine and an oxidizing agent, such as hydrogen peroxide.

Useful water soluble amine oxide surfactants are selected from the octyl, decyl, dodecyl, isododecyl, coconut, or tallow alkyl di-(lower alkyl) amine oxides, specific examples of which are octyldimethylamine oxide, nonyldimethylamine oxide, decyldimethylamine oxide, undecyldimethylamine oxide, dodecyldimethylamine oxide, iso-dodecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl)amine oxide, 3,6,9-trioctadecyldimethylamine oxide and 3-dodecoxy-2-hydroxypropyldi-(2-hydroxyethyl)amine oxide.

Anionic Surfactants

Anionic sulfate surfactants suitable for use in the present compositions include alkyl ether sulfates, alkyl sulfates, the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl) glucamine sulfates, and sulfates of alkylpolysaccharides such as the sulfates of alkylpolyglucoside, and the like. Also included are the alkyl sulfates, alkyl poly(ethyleneoxy) ether sulfates and aromatic poly(ethyleneoxy) sulfates such as the sulfates or condensation products of ethylene oxide and nonyl phenol (usually having 1 to 6 oxyethylene groups per molecule).

Anionic sulfonate surfactants suitable for use in the present compositions also include alkyl sulfonates, the linear and branched primary and secondary alkyl sulfonates, and the aromatic sulfonates with or without substituents.

Anionic carboxylate surfactants suitable for use in the present compositions include carboxylic acids (and salts), such as alkanoic acids (and alkanoates), ester carboxylic acids (e.g. alkyl succinates), ether carboxylic acids, and the like. Such carboxylates include alkyl ethoxy carboxylates, alkyl aryl ethoxy carboxylates, alkyl polyethoxy polycarboxylate surfactants and soaps (e.g. alkyl carboxyls). Secondary carboxylates useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary carboxylate surfactants typically contain no ether linkages, no ester linkages and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present. Suitable carboxylates also include acylamino acids (and salts), such as acylglutamates, acyl peptides, sarcosinates (e.g. N-acyl sarcosinates), taurates (e.g. N-acyl taurates and fatty acid amides of methyl tauride), and the like.

Suitable anionic surfactants include alkyl or alkylaryl ethoxy carboxylates of the following formula:

$$R—O—(CH_2CH_2O)_n(CH_2)_m—CO_2X \qquad (3)$$

in which R is a $C_8$ to $C_{22}$ alkyl group or

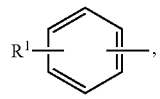

in which $R^1$ is a $C_4$-$C_{16}$ alkyl group; n is an integer of 1-20; m is an integer of 1-3; and X is a counter ion, such as hydrogen, sodium, potassium, lithium, ammonium, or an amine salt such as monoethanolamine, diethanolamine or triethanolamine. In some embodiments, n is an integer of 4 to 10 and m is 1. In some embodiments, R is a $C_8$-$C_{16}$ alkyl group. In some embodiments, R is a $C_{12}$-$C_{14}$ alkyl group, n is 4, and m is 1. In other embodiments, R is

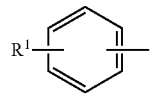

and $R^1$ is a $C_6$-$C_{12}$ alkyl group. In still yet other embodiments, $R^1$ is a $C_9$ alkyl group, n is 10 and m is 1.

Such alkyl and alkylaryl ethoxy carboxylates are commercially available. These ethoxy carboxylates are typically available as the acid forms, which can be readily converted to the anionic or salt form. Commercially available carboxylates include, Neodox 23-4, a $C_{12-13}$ alkyl polyethoxy (4) carboxylic acid (Shell Chemical), and Emcol CNP-110, a $C_9$ alkylaryl polyethoxy (10) carboxylic acid (Witco Chemical). Carboxylates are also available from Clariant, e.g. the product Sandopan® DTC, a $C_{13}$ alkyl polyethoxy (7) carboxylic acid.

Amphoteric Surfactants

Amphoteric, or ampholytic, surfactants contain both a basic and an acidic hydrophilic group and an organic hydrophobic group. These ionic entities may be any of anionic or cationic groups described herein for other types of surfactants. A basic nitrogen and an acidic carboxylate group are the typical functional groups employed as the basic and acidic hydrophilic groups. In a few surfactants, sulfonate, sulfate, phosphonate or phosphate provide the negative charge.

Amphoteric surfactants can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group, e.g., carboxy, sulfo, sulfato, phosphato, or phosphono. Amphoteric surfactants are subdivided into two major classes known to those of skill in the art and described in "Surfactant Encyclopedia" Cosmetics & Toiletries, Vol. 104 (2) 69-71 (1989), which is herein incorporated by reference in its entirety. The first class includes acyl/dialkyl ethylenediamine derivatives (e.g. 2-alkyl hydroxyethyl imidazoline derivatives) and their salts. The second class includes N-alkylamino acids and their salts. Some amphoteric surfactants can be envisioned as fitting into both classes.

Amphoteric surfactants can be synthesized by methods known to those of skill in the art. For example, 2-alkyl hydroxyethyl imidazoline is synthesized by condensation and ring closure of a long chain carboxylic acid (or a derivative) with dialkyl ethylenediamine. Commercial amphoteric surfactants are derivatized by subsequent hydrolysis and ring-opening of the imidazoline ring by alkylation—for example with chloroacetic acid or ethyl acetate. During alkylation, one or two carboxy-alkyl groups react to form a tertiary amine and an ether linkage with differing alkylating agents yielding different tertiary amines.

Long chain imidazole derivatives having application in the present invention generally have the general formula:

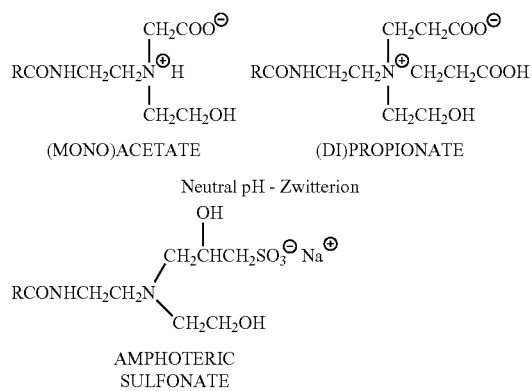

wherein R is an acyclic hydrophobic group containing from about 8 to 18 carbon atoms and M is a cation to neutralize the charge of the anion, generally sodium. Commercially prominent imidazoline-derived amphoterics that can be employed in the present compositions include for example: Cocoamphopropionate, Cocoamphocarboxy-propionate, Cocoamphoglycinate, Cocoamphocarboxy-glycinate, Cocoamphopropyl-sulfonate, and Cocoamphocarboxy-propionic acid. Amphocarboxylic acids can be produced from fatty imidazolines in which the dicarboxylic acid functionality of the amphodicarboxylic acid is diacetic acid and/or dipropionic acid.

The carboxymethylated compounds (glycinates) described herein above frequently are called betaines. Betaines are a special class of amphoteric discussed herein below in the section entitled, Zwitterion Surfactants.

Long chain N-alkylamino acids are readily prepared by reaction $RNH_2$, in which $R=C_8-C_{18}$ straight or branched chain alkyl, fatty amines with halogenated carboxylic acids. Alkylation of the primary amino groups of an amino acid leads to secondary and tertiary amines. Alkyl substituents may have additional amino groups that provide more than one reactive nitrogen center. Most commercial N-alkylamine acids are alkyl derivatives of beta-alanine or beta-N(2-carboxyethyl) alanine Examples of commercial N-alkylamino acid ampholytes having application in this invention include alkyl beta-amino dipropionates, $RN(C_2H_4COOM)_2$ and $RNHC_2H_4COOM$. In an embodiment, R can be an acyclic hydrophobic group containing from about 8 to about 18 carbon atoms, and M is a cation to neutralize the charge of the anion.

Suitable amphoteric surfactants include those derived from coconut products such as coconut oil or coconut fatty acid. Additional suitable coconut derived surfactants include as part of their structure an ethylenediamine moiety, an alkanolamide moiety, an amino acid moiety, e.g., glycine, or a combination thereof; and an aliphatic substituent of from about 8 to 18 (e.g., 12) carbon atoms. Such a surfactant can also be considered an alkyl amphodicarboxylic acid. These amphoteric surfactants can include chemical structures represented as: $C_{12}$-alkyl-$C(O)$—NH—$CH_2$—$CH_2$—$N^+(CH_2$—$CH_2$—$CO_2Na)_2$—$CH_2$—$CH_2$—OH or $C_{12}$-alkyl-$C(O)$—N(H)—$CH_2$—$CH_2$—$N^+(CH_2$—$CO_2Na)_2$—$CH_2$—$CH_2$—OH.

Disodium cocoampho dipropionate is one suitable amphoteric surfactant and is commercially available under the tradename Miranol™ FBS from Rhodia Inc., Cranbury, N.J. Another suitable coconut derived amphoteric surfactant with the chemical name disodium cocoampho diacetate is sold under the tradename Mirataine™ JCHA, also from Rhodia Inc., Cranbury, N.J.

A typical listing of amphoteric classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

Cationic Surfactants

Surface active substances are classified as cationic if the charge on the hydrotrope portion of the molecule is positive. Surfactants in which the hydrotrope carries no charge unless the pH is lowered close to neutrality or lower, but which are then cationic (e.g. alkyl amines), are also included in this group. In theory, cationic surfactants may be synthesized from any combination of elements containing an "onium" structure $R_nX+Y$— and could include compounds other than nitrogen (ammonium) such as phosphorus (phosphonium) and sulfur (sulfonium). In practice, the cationic surfactant field is dominated by nitrogen containing compounds, probably because synthetic routes to nitrogenous cationics are simple and straightforward and give high yields of product, which can make them less expensive.

Cationic surfactants preferably include, more preferably refer to, compounds containing at least one long carbon chain hydrophobic group and at least one positively charged nitrogen. The long carbon chain group may be attached directly to the nitrogen atom by simple substitution; or more preferably indirectly by a bridging functional group or groups in so-called interrupted alkylamines and amido amines. Such functional groups can make the molecule more hydrophilic and/or more water dispersible, more easily water solubilized by co-surfactant mixtures, and/or water soluble. For increased water solubility, additional primary, secondary or tertiary amino groups can be introduced or the amino nitrogen can be quaternized with low molecular weight alkyl groups. Further, the nitrogen can be a part of branched or straight chain moiety of varying degrees of unsaturation or of a saturated or unsaturated heterocyclic ring. In addition, cationic surfactants may contain complex linkages having more than one cationic nitrogen atom.

The surfactant compounds classified as amine oxides, amphoterics and zwitterions are themselves typically cationic in near neutral to acidic pH solutions and can overlap surfactant classifications. Polyoxyethylated cationic surfactants generally behave like nonionic surfactants in alkaline solution and like cationic surfactants in acidic solution.

The simplest cationic amines, amine salts and quaternary ammonium compounds can be schematically drawn thus:

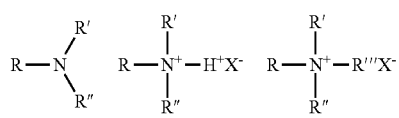

in which, R represents a long alkyl chain, R', R", and R''' may be either long alkyl chains or smaller alkyl or aryl groups or hydrogen and X represents an anion. In some embodiments of the invention, X is not a halide. The amine salts and quaternary ammonium compounds are preferred for practical use in this invention due to their high degree of water solubility.

The majority of large volume commercial cationic surfactants can be subdivided into four major classes and additional sub-groups known to those or skill in the art and described in "Surfactant Encyclopedia", *Cosmetics & Toiletries*, Vol. 104 (2) 86-96 (1989). The first class includes alkylamines and their salts. The second class includes alkyl imidazolines. The third class includes ethoxylated amines. The fourth class includes quaternaries, such as alkylbenzyldimethylammonium salts, alkyl benzene salts, heterocyclic ammonium salts, tetra alkylammonium salts, and the like. Cationic surfactants are known to have a variety of properties that can be beneficial in the present compositions. These desirable properties can include detergency in compositions of or below neutral pH, antimicrobial efficacy, thickening or gelling in cooperation with other agents, and the like.

Cationic surfactants useful in the compositions of the present invention include those having the formula $R^1_m R^2_x Y_L Z$ wherein each $R^1$ is an organic group containing a straight or branched alkyl or alkenyl group optionally substituted with up to three phenyl or hydroxy groups and optionally interrupted by up to four of the following structures:

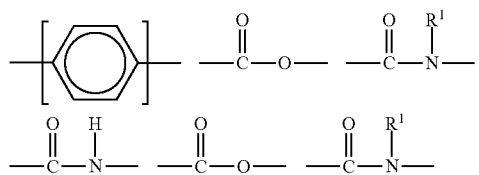

or an isomer or mixture of these structures, and which contains from about 8 to 22 carbon atoms. The $R^1$ groups can additionally contain up to 12 ethoxy groups. m is a number from 1 to 3. Preferably, no more than one $R^1$ group in a molecule has 16 or more carbon atoms when m is 2 or more than 12 carbon atoms when m is 3. Each $R^2$ is an alkyl or hydroxyalkyl group containing from 1 to 4 carbon atoms or a benzyl group with no more than one $R^2$ in a molecule being benzyl, and x is a number from 0 to 11, preferably from 0 to 6. The remainder of any carbon atom positions on the Y group are filled by hydrogens. Y is can be a group including, but not limited to:

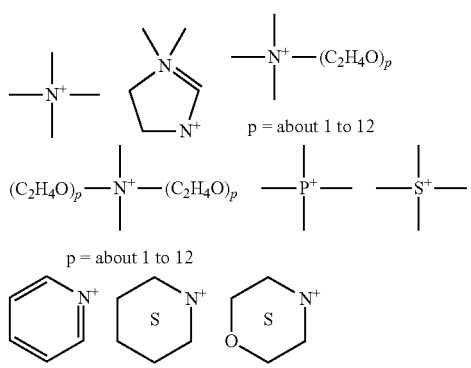

or a mixture thereof. Preferably, L is 1 or 2, with the Y groups being separated by a moiety selected from $R^1$ and $R^2$ analogs (preferably alkylene or alkenylene) having from 1 to about 22 carbon atoms and two free carbon single bonds when L is 2. Z is a water soluble anion, such as a halide, sulfate, methylsulfate, hydroxide, or nitrate anion, particularly preferred being chloride, bromide, iodide, sulfate or methyl sulfate anions, in a number to give electrical neutrality of the cationic component.

Additional Functional Ingredients

In some embodiments, the compositions of the present invention can include additional functional ingredients. Additional functional ingredients suitable for use with the compositions of the present invention include, but are not limited to, acidulants, additional stabilizing agents, e.g., chelating agents, sequestrants and/or crystallization inhibitors, buffers, detergents, wetting agents, defoaming agents, hydrotropes, thickeners, foaming agents, threshold agents, aesthetic enhancing agents (i.e., colorants, odorants, or perfumes) and other cleaning agents. These additional ingredients can be preformulated with the compositions of the invention or added to the system before, after, or substantially simultaneously with the addition of the compositions of the present invention.

Sequestrants and Chelating Agents

In some embodiments, the peroxycarboxylic acid compositions may include sequestrants and/or chelating agents to stabilize the compositions. Organic sequestering and chelating agents are particularly suitable for use according to the invention and may include both polymeric and small molecule agents. The polymeric sequestrants commonly include polyanionic compositions, such as polyacrylic acid compounds. According to the invention, polyanionic compounds should not be oxidizable by the peracid and/or hydrogen peroxide of the compositions.

Organic small molecule agents include organocarboxylate compounds or organophosphate agents. Exemplary small molecule organic agents include ethylenediaminetriacetic acid (EDTA), diethylenetriaminepentaacetic acid (DTPA), N-hydroxyethylenediaminetriacetic acid (HEDTA), nitrolotriacetic acid (NTA), methylglycinediacetic acid (MGDA), tetrasodium L-glutamic acid, N,N-diacetic acid (GLDA), triethylenetetraaminehexaacetic acid (TTHA), and the respective alkali metal, ammonium and substituted ammonium salts thereof.

Phosphates and aminophosphonates may also be also suitable for use with the compositions, including ethylenediaminetetramethylene phosphonates, nitrilotrismethylene phosphonates, 1-hydroxy ethylidene-1,1-diphosphonates, diethylenetriamine-pentamethylene phosphonate, and 2-phosphonobutane-1,2,4-tricarboxylates, for example. Alternative suitable sequestrants include water soluble polycarboxylate polymers, including homopolymeric and copolymeric agents such as polymeric compositions with pendant (—COOH) carboxylic acid groups, including polyacrylic acid, polymethacrylic acid, polymaleic acid, acrylic acid-methacrylic acid copolymers, acrylic-maleic copolymers, hydrolyzed polyacrylamide, hydrolyzed methacrylamide, hydrolyzed acrylamide-methacrylamide copolymers, hydrolyzed polyacrylonitrile, hydrolyzed polymethacrylonitrile, hydrolyzed acrylonitrile methacrylonitrile copolymers, or mixtures thereof. Water soluble salts or partial salts of these polymers or copolymers such as their respective alkali metal or ammonium salts may also be used. The weight average molecular weight of the polymers is from about 4,000 to about 12,000. These and other sequestrants and/or chelating agents known in the art may be employed in the peroxycarboxylic acid compositions.

Exemplary Compositions

Various embodiments of the invention are shown in Table depicting exemplary ranges of the treated peroxycarboxylic acid compositions according to the invention.

TABLE 1

| | Wt-% | Wt-% | Wt-% | Wt-% |
| --- | --- | --- | --- | --- |
| Peracid | 0.01-80 | 0.1-50 | 1-30 | 5-30 |
| Carboxylic Acid | 0.01-80 | 0.1-50 | 1-30 | 1-15 |
| Oxidizing Agent | 0-15 | 0-10 | 0-8 | 0-5 |
| Surfactant | 0-50 | 0-30 | 0-20 | 0-15 |
| Additional Functional Ingredients | 0-50 | 0-20 | 0-10 | 0-15 |
| Water | 0-50 | 0-30 | 0-20 | 0-15 |

The use of the active oxygen coordinating compound according to the invention provides a reduced hydrogen peroxide containing peroxycarboxylic acid composition having a shelf-stability of at least about 24 hours, preferably at least a few days, and more preferably at least about 30 days. In still further aspects, the reduced hydrogen peroxide compositions have a shelf-stability of at least about 3 months, more preferably at least about 1 year, or more. In an aspect, the shelf-stability of the reduced hydrogen peroxide compositions are demonstrated by not exhibiting more than about 10 wt-% peracid decomposition for at least about 24 hours, preferably at least a few days, and more preferably at least about 30 days. In a preferred aspect, the shelf-stability of the reduced hydrogen peroxide compositions are demonstrated by having less than about 5 wt-% peracid decomposition, preferably less than about 1 wt-% decomposition, and still more preferably substantially no or no decomposition for the same periods of time.

As one skilled in the art shall appreciate based on the disclosure of the present invention, the reduced hydrogen peroxide containing peroxycarboxylic acid compositions of the invention can be formulated as a liquid concentrate composition and/or use compositions. In addition, the reduced hydrogen peroxide containing peroxycarboxylic acid compositions can further be employed in various forms, including for example, gels, aerosols, a gas, a wax, solids, powders, or as solutions or suspensions.

In an aspect, the treated peroxycarboxylic acid compositions do not have a significantly altered pH from the original peracid composition. Beneficially, as a result of the maintained level of the carboxylic acids and the peroxycarboxylic acids of the peroxycarboxylic acid compositions the pH of the treated compositions remain largely unchanged. Typically, the pH of an equilibrium peracid mixture is less than about 1 or about 2, and wherein the pH of a 1% solution of the equilibrium mixture in water is about 2 to about 9, depending on the other components of the 1% solution, and the pH of a use composition can be from about 1 to about 9 depending on the other components. Preferably, compositions treated to reduce the hydrogen peroxide content according to the invention have a pH less than about 7, or from about 1 to 7. In an aspect, the treated peroxycarboxylic acid compositions undergo a pH change of less than about 1 pH unit, preferably less than about 0.5 pH units according to the methods of the invention. It is to be understood that all ranges and values between these ranges and values are encompassed by the present invention.

In an aspect of the invention, the treated peroxycarboxylic acid compositions have improved antimicrobial efficacy over conventional, equilibrium peroxycarboxylic acid compositions as a result of the reduced hydrogen peroxide content of the compositions.

Methods of Removing Hydrogen Peroxide

Peroxycarboxylic acid compositions are generated having reduced hydrogen peroxide (or other oxidizing agent) percent actives and enhanced antimicrobial efficacy according to the methods of the invention. The methods of reducing hydrogen peroxide from a peroxycarboxylic acid composition may comprise, consist of and/or consist essentially of providing an aqueous peracid composition to be treated and contacting the peracid composition with an active oxygen coordinating compound. The methods may optionally further comprise, consist of and/or consist essentially of additional further contacting steps wherein the peracid composition is again contacted with the active oxygen coordinating compound. The methods may further comprise the generation of a solid stable form of oxygen bleach as a by-product of the methods, which is suitable for use as a bleaching agent.

Providing Peroxycarboxylic Acid Compositions

The step of first providing a peroxycarboxylic acid composition may employ either a use solution or a concentrated peroxycarboxylic acid composition according to the invention. Preferably, a concentrated peroxycarboxylic acid composition is employed. Preferably, an undiluted peroxycarboxylic acid composition is employed.

In some aspects, concentrated peroxycarboxylic acid compositions having a percent active peroxycarboxylic acid up to about 5 wt-% are employed. In further aspects more concentrated peroxycarboxylic acid compositions having up to about 10 wt-% active peroxycarboxylic acid, up to about 12 wt-% active peroxycarboxylic acid, or up to about 15 wt-% active peroxycarboxylic acid are employed. In still further aspects, concentrated peroxycarboxylic acid compositions having a percent active peroxycarboxylic acid up to or greater than about 15 wt-% are employed. Notably, the method step of providing a concentrate or undiluted aqueous peroxycarboxylic acid composition is distinct from the prior methods for removing hydrogen peroxide using enzymes, which are suitable only for the treatment of dilute concentrations of peroxycarboxylic acid compositions.

A concentrate composition employed for the methods of the invention can subsequently be diluted, for example with water, to form a use composition of the reduced hydrogen peroxide peroxycarboxylic acid composition. In an embodiment, a concentrate composition can be treated according to the invention with the active oxygen coordinating compound and thereafter diluted to a use solution before to application to an object. Primarily for reasons of economics, the concentrate can be marketed and an end user can dilute the concentrate with water or an aqueous diluent to a use solution.

The level of active components (and percent actives) in the concentrate composition is dependent on the intended dilution factor and the desired activity of the peroxycarboxylic acid composition. Generally, a dilution of about 1 fluid ounce to about 10 gallons of water to about 10 fluid ounces to about 1 gallon of water is used for aqueous compositions of the present invention. In some embodiments, higher use dilutions can be employed if elevated use temperature or extended exposure time (greater than 30 seconds) can be employed. In the typical use locus, the concentrate is diluted with a major proportion of water using commonly available tap or service water mixing the materials at a dilution ratio of about 3 to about 40 ounces of concentrate per 100 gallons of water.

In some embodiments, such as use in laundry applications, the concentrated compositions can be diluted at a dilution ratio of about 0.1 g/L to about 100 g/L concentrate to diluent, about 0.5 g/L to about 10.0 g/L concentrate to diluent, about 1.0 g/L to about 4.0 g/L concentrate to diluent, or about 1.0 g/L to about 2.0 g/L concentrate to diluent. In other embodiments, a use composition can include about 0.01 to about 10 wt-% of a concentrate composition and about 90 to about 99.99 wt-% diluent; or about 0.1 to about 1 wt-% of a concentrate composition and about 99 to about 99.9 wt-% diluent. Amounts of an ingredient in a use composition can be calculated from the amounts listed above for concentrate compositions and these dilution factors.

One skilled in the art will ascertain from the disclosure of the invention that the dilution of the peroxycarboxylic acid compositions may occur before or after contacting the peroxycarboxylic acid composition with the active oxygen coordinating compound.

Contacting the Active Oxygen Coordinating Compound

In a preferred aspect, the peroxycarboxylic acid composition contacts (or is treated with) the active oxygen coordinating compound. In a preferred aspect, the active oxygen coordinating compound is selected from the group consisting of urea, a urea copolymer and/or derivative (such as a urea acid salt), polyvinylpyrrolidone (PVP), a PVP copolymer and/or derivative (such as a PVP acid salt), an inorganic carbonate, and combinations of the same. In a preferred aspect the active oxygen coordinating compound is a solid.

The contacting of the peroxycarboxylic acid composition with the active oxygen coordinating compound may occur through the direct application of the peroxycarboxylic acid composition to a source of active oxygen coordinating compound. The contacting can include, for example, the spraying of the peroxycarboxylic acid composition over the coordinating compound substrate, such as for example using a spray nozzle to spray the solution at a particular rate or flow over the active oxygen coordinating compound substrate in a vertical, horizontal or downward flow.

A suitable feed rate for contacting the peroxycarboxylic acid composition with the active oxygen coordinating compound will vary depending upon numerous factors, including for example, the amount of the active oxygen coordinating compound employed, amount of peroxycarboxylic acid composition to be treated, the configurations of the substrate for the active oxygen coordinating compound (e.g. geometric and other configurations). One skilled in the art will make adjustments to the feed rate for contacting the peroxycarboxylic acid composition with the active oxygen coordinating compound based upon such factors.

In a preferred aspect, the active oxygen coordinating compound is a solid that is affixed, packed into or otherwise bound to or contained within a column, cartridge, filter or other substrate. In such embodiments, the aqueous concentrate or diluted peroxycarboxylic acid composition passes through the column, cartridge, filter or other substrate in order to contact the peroxycarboxylic acid composition with the active oxygen coordinating compound. In an embodiment, the aqueous concentrate or diluted peroxycarboxylic acid composition may be pumped or eluted through the column, cartridge, filter or other substrate in order to contact the peroxycarboxylic acid composition with the active oxygen coordinating compound.

In a further aspect, the substrates may employ additional agents, including for example, silicon dioxide, titanium dioxide, aluminum oxide, zinc oxide and the like.

In an aspect, an aqueous peroxycarboxylic acid composition is passed through the column, cartridge, filter or other substrate containing the active oxygen coordinating compound, such as urea, wherein the weight ratio of the peroxycarboxylic acid to the active oxygen coordinating compound is from about 1:1 to about 1:10, preferably from about 1:1 to about 1:4, and more preferably about 1:1 to about 1:2. Without being limited according to the invention, all ranges recited are inclusive of the numbers defining the range and include each integer within the defined range.

In an aspect, the contact time required for the removal of hydrogen peroxide by the active oxygen coordinating compound may range from a few seconds to a few hours, preferably from a few seconds to about 30 minutes, preferably from about one minute to about 15 minutes, preferably from about one minute to about five minutes. Without being limited according to the invention, all ranges recited are inclusive of the numbers defining the range and include each integer within the defined range.

In some aspects, the methods of removing hydrogen peroxide may be completed by a single step of contacting the peroxycarboxylic acid composition to the active oxygen coordinating compound (e.g. running the peracid composition through a solid urea column a single time). In other aspects, the methods may include various contacting steps, including for example the re-pumping or recirculating of peroxycarboxylic acid composition through the active oxygen coordinating compound in the column, cartridge, filter or other form of the substrate.

In an optional embodiment, the contacting of the peroxycarboxylic acid composition to the active oxygen coordinating compound may further include a means of agitation or other mechanism to increase the contact between the two components. For example, the flow of the peroxycarboxylic acid composition through the column or other substrate containing the active oxygen coordinating compound may be adjusted to increase/decrease the rate to increase contact of the components, mechanical agitation may be employed, recirculation, and combinations thereof.

There are numerous benefits to the single step reduction and/or elimination of the hydrogen peroxide from the peroxycarboxylic acid composition according to the invention. For example, the methods of the invention do not require various steps of solubilization, dehydration/drying, distillation, vaporization and/or filtration as set forth in various methods known in the art. See e.g., GP1501823(Hofen et al.) and GB1518227 (Prescher et al.), which are herein incorporated by reference in their entirety. Beneficially, according to the invention there is no dehydration/drying, distillation, vaporization and/or filtration steps required. In addition, the methods do not require the use of additional solvents. The single-step processes according to the invention simplifies the process, reduces costs, and still further beneficially results in the formation of a reusable active bleach component (e.g. urea-hydrogen peroxide bleach complex).

Beneficially, the oxygen coordinating compound both selectively and nondestructively removes hydrogen peroxide. In an aspect, the concentration or percent actives of peroxycarboxylic acids in the treated peroxycarboxylic acid composition remains substantially unchanged. For example, no more than about 5 wt-%, about 10 wt-%, about 20 wt-%, about 25 wt-%, about 30 wt-% or more of the peroxycarboxylic acid is removed from the treated composition. As a result, the treated peroxycarboxylic acid composition has a significant amount of the hydrogen peroxide removed while having a minimal effect on the peracid level.

In a further beneficial aspect of the invention, the contacting step can occur at a point of manufacture as opposed to a point of use. Without being limited to a particular theory of the invention, the use of concentrated peroxycarboxylic acid compositions to be contacted with the active oxygen coordinated compound provides a longer stability of the reduced hydrogen peroxide composition. As a matter of economics this is further preferred due to the ability to transport the concentrated or undiluted reduced hydrogen peroxide peroxycarboxylic acid compositions. In addition, this is further beneficial for the end user who is not required to conduct the additional step of contacting the peroxycarboxylic acid composition with the active oxygen coordinating compound at a point of use. However, in an alternative aspect, the contacting step could occur at a point of use by an end user.

The methods of the invention are suitable for use according to a broad temperature range. Beneficially, the step of contacting the peracid with the active oxygen coordinating compound may occur at a temperature range from about 10 to 70° C., preferably about 20 to 60° C.

A further beneficial aspect of the methods of the invention include the effect of the active oxygen coordinating compound on the malodors associated with the peroxycarboxylic acid compound. In an aspect of the invention, the methods may further provide beneficial effects on the odor of the peroxycarboxylic acid compositions as a result of the active oxygen coordinating compound having beneficial odor reducing efficacy, as disclosed in related application U.S. Ser. No. 13/661,312, filed simultaneously herewith, which is incorporated by reference herein in its entirety. For example, in an embodiment of the invention wherein a portion of the active oxygen coordinating compound is dissolved into the peroxycarboxylic acid composition there would be expected a beneficial effect of reduced peracid odor.

Generating a Coordinated Hydrogen Peroxide Compound

Beneficially, the methods of the invention generate a raw material for further bleaching applications. According to the invention, the contacting of the peroxycarboxylic acid composition with the active oxygen coordinating compound results in the selective coordination of the hydrogen peroxide to the solid active oxygen coordinating compound substrate. The coordination is a selective and non-destructive means of removing the hydrogen peroxide from the peroxycarboxylic acid composition. For example, in an aspect of the invention wherein a urea substrate is employed as the active oxygen coordinating compound, the urea forms a solid, stable urea/hydrogen peroxide compound that can be employed for further bleaching efficacy. This creates a solid, recycled active bleach compound for subsequent use.

In an aspect, the generated solid active bleach compound is stable. In an embodiment, the generated solid active bleach compound has a shelf-stability of at least about 1 week, more preferably at least about 1 month, more preferably at least about 3 months, more preferably at least about 1 year, or more.

One skilled in the art will ascertain that the generated solid active bleach compound retains the expected and well-known bleaching efficacy.

In a further aspect, the weight ratios of the active oxygen coordinating compound to the hydrogen peroxide is generated in a fixed ratio which is dependent upon the particular materials employed. See e.g. disclosure of solid/powder compounds of hydrogen peroxide and PVP in U.S. Pat. Nos. 3,376,110 and 5,077,047, which is incorporated herein by reference in its entirety. Beneficially, the formation of the raw bleaching material does not require any additional steps in the process according to the invention. In particular, the generation of the solid urea/hydrogen peroxide compound does not require any active drying, dehydration, atomizing and/or filtration steps. In addition, the generation of the solid urea/hydrogen peroxide compound does not require use of any additional polymers and/or solvents (e.g. organic solvents). In an aspect of the invention, the generated raw bleaching material is ready to use, however a rinse step may be employed for applications of use which do not require acidity for bleaching efficacy. As one skilled in the art will ascertain, a rinse step is not required.

The amount of hydrogen peroxide in the solid urea (or other active oxygen coordinating compound) and hydrogen peroxide complex can vary, from about at least 7.5 wt-%, at least 10 wt-%, at least 12.5 wt-%, at least 15 wt-%, at least 20 wt-%, or greater. In addition, without being limited according to the invention, all ranges recited are inclusive of the numbers defining the range and include each integer within the defined range.

One skilled in the art will ascertain according to the description of the invention that the non-destructive removal of the hydrogen peroxide from the peroxycarboxylic acid composition results in formation of a compound with bleaching efficacy afforded by both the oxidizing agent hydrogen peroxide and the active oxygen coordinating compound substrate, e.g. urea. This is distinct from the prior methods of enzymatically removing hydrogen peroxide, which results in the destruction of the hydrogen peroxide. Therefore, it is both unexpected and beneficial that according to the methods of the invention a raw material is generated that has independent bleaching activity from the treated peracid composition. According to the methods of the invention a solid stable form of oxygen bleach is generated.

Methods of Use

According to one embodiment of the invention, the treated peroxycarboxylic acid compositions are employed for antimicrobial and/or bleaching activity. The compositions of the present invention can be used as antimicrobial and/or bleaching compositions for a variety of substrates and surfaces, e.g., textiles and hard surfaces. The compositions of the present invention can also be used as antimicrobial, disinfectant and/or sanitizer compositions. Preferably the compositions are particularly suitable for use at acid or neutral pHs. According to the invention, the methods of using the compositions employ compositions having a pH from about 1 to about 9, preferably from about 1 to about 7.

The compositions may be used for various applications, e.g., food processing plant biocidal treatments, food contact sanitizing, hard surface disinfection and biocidal activity, including large architectural surfaces, plant sanitizing, ware wash bleaching and biocidal activity, and textile disinfection, including laundry biocidal activity and/or bleaching, souring and/or sanitizing. In some embodiments, compositions containing compounds of the present invention can be multipurpose. That is, the compositions of the present invention can, for example, act as both antimicrobials, biocides and bleaches. The compositions of the present invention can further act as disinfection, a combination of disinfection and cleaning, virucidal treatment and/or fungicidal treatment.

According to an embodiment of the invention, a method for reducing a microbial population on a variety of surfaces, and a method for bleaching a variety of surfaces are provided. The methods according to the invention can operate on an object, article, surface, or the like, by contacting the object, article or surface with the treated peroxycarboxylic acid composition of the invention having reduced hydrogen peroxide concentration. As one skilled in the art shall ascertain based upon the disclosure of the present invention, contacting can include any of numerous methods for applying a composition, such as spraying the composition, immersing the object in the composition, foam or gel treating the object with the composition, or a combination thereof.

In a further embodiment, the peroxycarboxylic acid compositions can be employed in a variety of health care, laundry care, ware wash applications, food processing and consumer use applications.

The reduced hydrogen peroxide peroxycarboxylic acid compositions can be employed for reducing the population of various pathogenic microorganisms, such as pathogens of humans, animals, and the like. The peroxycarboxylic acid compositions have activity against a variety of pathogens, including Gram positive (for example, *Listeria monocytogenes* or *Staphylococcus aureus*) and Gram negative (for example, *Escherichia coli* or *Pseudomonas aeruginosa*) bacteria, yeast, molds, bacterial spores, viruses, etc. fungi, molds, bacteria, spores (e.g. endospores), and viruses. Such pathogens can cause a variety of diseases and disorders. As a result of the activity of the peroxycarboxylic acid compositions, they can be used as or included in products such as sterilants, sanitizers, disinfectants, preservatives, deodorizers, antiseptics, fungicides, germicides, sporicides, virucides, detergents, bleaches, hard surface cleaners, and pre- or post-surgical scrubs.

According to an embodiment of the invention, the reduced hydrogen peroxide peroxycarboxylic acid compositions are utilized to kill one or more of the food-borne pathogenic bacteria associated with a food product and/or food processing methods and applications, including, but not limited to, *Salmonella, Campylobacter, Listeria, Escherichia coli*, yeast, and mold.

According to further embodiments, the reduced hydrogen peroxide peroxycarboxylic acid compositions are utilized to kill one or more of the pathogenic bacteria associated with a health care surfaces and environments including, but not limited to, *Salmonella, Staphylococcus*, including methicillin resistant *Staphylococcus aureus, Salmonella, Pseudomonas, Escherichia*, mycobacteria, yeast, and mold. In still other embodiments of the invention, the reduced hydrogen peroxide peroxycarboxylic acid compositions are utilized to kill one or more of the pathogenic agents, including bacteria, associated with water processing and/or treatment applications.

A concentrate or use concentration of the reduced hydrogen peroxide peroxycarboxylic acid compositions can be applied to or brought into contact with an object or surface by any conventional method or apparatus for applying an antimicrobial or bleaching composition to an object or surface. For example, the object can be wiped with, sprayed with, and/or immersed in the peracid composition, or a use composition made from the peracid composition. Contacting can be manual or by machine which may employ a liquid, gel, aerosol, gas, wax, solid, or powdered peracid compositions according to the invention, or solutions containing these compositions.

According to an embodiment of the invention, upon application of the reduced hydrogen peroxide peroxycarboxylic acid compositions the object, article or surface may be moved with mechanical action, preferably agitated, rubbed, brushed, etc. Agitation can be by physical scrubbing, through the action of the spray solution under pressure, through sonication, or by other methods. Agitation increases the efficacy of the spray solution in killing micro-organisms, perhaps due to better exposure of the solution into the crevasses or small colonies containing the micro-organisms. According to further embodiments of the invention a use solution of the reduced hydrogen peroxide peroxycarboxylic acid composition can also be used at a temperature of about 10 to 70° C., preferably about 20 to 60° C. to increase efficacy.

A sprayed reduced hydrogen peroxide peroxycarboxylic acid composition can be left on a treated object or surface for a sufficient amount of time to suitably reduce the population of microorganisms, and then rinsed, drained and/or evaporated off the treated object or surface. The present methods require a certain minimal contact time of the peracid composition for occurrence of significant antimicrobial effect. The contact time can vary with concentration of the use composition, method of applying the use composition, temperature of the use composition, amount of soil on the treated object or surface, number of microorganisms on the treated object or surface, type of antimicrobial agent, or the like. Preferably the exposure time is at least about 5 to about 15 seconds.

Immersing an object or surface in a liquid reduced hydrogen peroxide peroxycarboxylic acid composition can be accomplished by any of a variety of methods known to those of skill in the art. For example, the object can be placed into a tank or bath containing the reduced hydrogen peroxide peroxycarboxylic acid composition. Alternatively, the object can be transported or processed in a flume of the reduced hydrogen peroxide peroxycarboxylic acid composition. The washing solution is preferably agitated to increase the efficacy of the solution and the speed at which the solution reduces micro-organisms accompanying the object. Agitation can be obtained by conventional methods, including ultrasonics, aeration by bubbling air through the solution, by mechanical methods, such as strainers, paddles, brushes, pump driven liquid jets, or by combinations of these methods. The washing solution can be heated to increase the efficacy of the solution in killing micro-organisms. After the object has been immersed for a time sufficient for the desired antimicrobial and/or bleaching effect, the object can be removed from the bath or flume and the peracid composition can be rinsed, drained, or evaporated off the object.

Methods for Industrial Processing

In some aspects, the invention includes methods of using the reduced hydrogen peroxide peroxycarboxylic acid compositions to prevent biological fouling in various industrial processes and industries, including oil and gas operations, to control microorganism growth, eliminate microbial contamination, limit or prevent biological fouling in liquid systems, process waters or on the surfaces of equipment that come in contact with such liquid systems. As referred to herein, microbial contamination can occur in various industrial liquid systems including, but not limited to, air-borne contamination, water make-up, process leaks and improperly cleaned equipment. In another aspect, the peroxycarboxylic acid compositions are used to control the growth of microorganisms in water used in various oil and gas operations. In a further aspect, the compositions are suitable for incorporating into fracturing fluids to control or eliminate microorganisms.

For the various industrial processes disclosed herein, "liquid system" refers to flood waters or an environment within at least one artificial artifact, containing a substantial amount of liquid that is capable of undergoing biological fouling, it includes but is not limited to industrial liquid systems, industrial water systems, liquid process streams, industrial liquid process streams, industrial process water systems, process water applications, process waters, utility waters, water used in manufacturing, water used in industrial services, aqueous liquid streams, liquid streams containing two or more liquid phases, and any combination thereof.

In at least one embodiment this technology would be applicable to any process or utility liquid system where microorganisms are known to grow and are an issue, and biocides are added. Examples of some industrial process water systems where the method of this invention could be applied are in process water applications (flume water, shower water, washers, thermal processing waters, brewing, fermentation, CIP (clean in place), hard surface sanitization, etc.), Ethanol/Biofuels process waters, pretreatment and utility waters (membrane systems, ion-exchange beds), water used in the process/manufacture of paper, ceiling tiles, fiber board, microelectronics, E-coat or electro deposition applications, process cleaning, oil exploration and energy services (completion and work over fluids, drilling additive fluids, fracturing fluids, flood waters, etc.; oil fields—oil and gas wells/flow line, water systems, gas systems, etc.), and in particular water systems where the installed process equipment exhibits lowered compatibility to halogenated biocides.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The contents of all references, patents, and patent applications cited throughout this application are hereby incorporated by reference to the same extent as if each individual publication or patent application was specifically and individually indicated as incorporated by reference. All publications and patent applications in this specification are indicative of the level of ordinary skill in the art to which this invention pertains. The invention is further illustrated by the following examples, which should not be construed as further limiting.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

The materials used in the following Examples are provided herein:

Oxonia Active®: an equilibrium peroxyacetic acid antimicrobial agent available from Ecolab Inc. (employed with titration to adjust concentration of peracid and hydrogen peroxide for examples of the invention).

Active oxygen coordinating agent: prilled urea.

Example 1

Measured aliquots of a concentrated peracetic acid composition containing about 10.5% peracetic acid, 27% hydrogen peroxide, acetic acid, and water were obtained. The concentrated peracetic acid composition was eluted through a column packed with about 200 grams prilled urea at ambient temperatures and using a gravity feed with a stopcock open on column. The eluent was then titrated for percent hydrogen peroxide and peracetic acid content. As shown in Table 2 the hydrogen peroxide levels of the peracetic acid compositions dropped from 27% to about 7% according to an embodiment of the invention.

Variations in the weight ratio of the peracetic acid composition to the urea were evaluated to determine ranges of ratios for the non-enzymatic, non-destructive, selected removal of hydrogen peroxide from the peracetic acid composition suitable for use according to the invention.

TABLE 2

| Weight Product:Urea Starting Material | % $H_2O_2$ | % Peracetic Acid |
|---|---|---|
| No urea | 27.0 | 10.5 |
| 1:1 | 7.6 | 7.4 |
| 1:2 | 7.4 | 6.2 |
| 1:4 | 7.4 | 6 |
| 1.5:1 | 12.6 | 7.4 |
| 2:1 | 14.3 | 7.5 |

The percentages of hydrogen peroxide and peracetic acid titrated from the treated peracetic acid composition samples were uncorrected for any urea which might have dissolved in the test sample. As is shown in Table 2, at ratios of at least 1 part urea to 1 part peracetic acid feedstock there is a substantial reduction of hydrogen peroxide content of the peracetic acid composition, while the corresponding peracetic acid level showed only a minimal decrease. Additional benefits may be obtained by increasing the ratio of the urea to peracetic acid composition, including for example weight ratios of from about 1:1 to about 4:1.

Beneficially, the urea column produced a urea/hydrogen peroxide compound that retained bleaching efficacy, demonstrating the non-destructive and selective removal of the hydrogen peroxide from the peracetic acid composition. The urea/hydrogen peroxide compound is a commercially-valuable bleach component that can be recycled and used in various bleaching applications.

The inventions being thus described, it will be obvious that the same may be varied in many ways. Such variations are not to be regarded as a departure from the spirit and scope of the inventions and all such modifications are intended to be included within the scope of the following claims.

What is claimed is:

1. A peroxycarboxylic acid composition having reduced hydrogen peroxide concentration comprising:
    from about 0.1-50 wt-% of at least one peroxycarboxylic acid;
    from about 0.1-50 wt-% of at least one carboxylic acid; and
    from about 0-5 wt-% hydrogen peroxide;
    wherein the composition is produced by the process of contacting an aqueous peroxycarboxylic acid composition with a non-enzymatic, non-destructive, solid active oxygen coordinating compound to reduce by at least about 80% and/or eliminate hydrogen peroxide from the composition altering an equilibrium of the peroxycarboxylic acid composition to have increased peroxycarboxylic acid in comparison to reduced or eliminated concentration of hydrogen peroxide,
    wherein the active oxygen coordinating compound is a non-enzymatic, nitrogen-containing compound that is provided in a weight ratio of the peroxycarboxylic acid to the active oxygen coordinating compound from about 1:1 to about 1:10.

2. The composition of claim 1, wherein the active oxygen coordinating compound is selected from the group consisting of urea, polyvinylpyrrolidone, inorganic carbonates and combinations thereof.

3. The composition of claim 2, wherein the active oxygen coordinating compound is selected from the group consisting of urea copolymers and/or derivatives, polyvinylpyrrolidone copolymers and/or derivatives, and combinations thereof.

4. The composition of claim 2, wherein the active oxygen coordinating compound is urea.

5. The composition of claim 1, wherein the at least one peroxycarboxylic acid is a sulfoperoxycarboxylic acid and/or an alkyl peroxycarboxylic acid.

6. The composition of claim 1, wherein the at least one peroxycarboxylic acid is a C1-C20 alkyl peroxycarboxylic acid.

7. The composition of claim 1, wherein the composition comprises from about 1-30 wt-% of at least one peroxycarboxylic acid, from about 1-30 wt-% of at least one carboxylic acid, and about 0 wt-% hydrogen peroxide.

8. The composition of claim 1, wherein the process of contacting the peroxycarboxylic acid composition with the solid active oxygen coordinating compound includes running the aqueous peroxycarboxylic acid composition over a column, cartridge, fluidized bed, filter or other substrate containing the active oxygen coordinating compound.

9. The composition of claim 1, wherein the process of contacting the peroxycarboxylic acid composition with the solid active oxygen coordinating compound generates a solid complex of the hydrogen peroxide and active oxygen coordinating compound suitable for use as a bleaching agent.

10. The composition of claim 1, further comprising a surfactant, a transition metal chelant, sequestrant, water and/or additional functional ingredients.

11. A method of reducing hydrogen peroxide from a peroxycarboxylic acid composition comprising:
    providing an aqueous peroxycarboxylic acid composition;
    contacting the aqueous peroxycarboxylic acid composition with a non-enzymatic, non-destructive, solid active oxygen coordinating compound to reduce the content of hydrogen peroxide by at least about 80% and to a concentration of from about 0-5 wt-%, wherein the reduction of said hydrogen peroxide alters an equilibrium of the peroxycarboxylic acid composition to have increased peroxycarboxylic acid in comparison to reduced or eliminated concentration of hydrogen peroxide; and
    generating a reusable solid complex of the hydrogen peroxide and active oxygen coordinating compound suitable for use as a bleaching agent, wherein the generated solid complex does not require use of organic solvents and/or dehydration and/or drying steps for generating the bleaching agent;
    wherein the active oxygen coordinating compound is a solid, non-enzymatic, non-destructive, nitrogen-containing compound, and wherein the ratio of the peroxycarboxylic acid to the active oxygen coordinating compound is from about 1:1 to about 1:10.

12. The method of claim 11, wherein the active oxygen coordinating compound is selected from the group consisting of urea, urea copolymers and/or derivatives, polyvinylpyrrolidone, polyvinylpyrrolidone copolymers and/or derivatives, inorganic carbonates and combinations thereof.

13. The method of claim 11, wherein the active oxygen coordinating compound is a solid urea.

14. The method of claim 11, wherein the active oxygen coordinating compound is contained within a column, cartridge, fluidized bed, filter or other substrate.

15. The method of claim 11, wherein the ratio of the peroxycarboxylic acid to the active oxygen coordinating compound is from about 1:1 to about 1:4 and removes at least about 25 wt-% of the hydrogen peroxide from the peroxycarboxylic acid composition.

16. The method of claim 11, wherein the aqueous peroxycarboxylic acid composition is a concentrate.

17. The method of claim 11, wherein the method has a minimal effect on the peroxycarboxylic acid concentration of the composition and removes less than about 25 wt-% of the peroxycarboxylic acid from the composition.

18. A method of reducing population of microorganism on an object, comprising:
    contacting an object with a reduced hydrogen peroxide peroxycarboxylic acid composition of claim 1.

19. The method of claim 18, wherein the object is a textile, food processing or manufacturing surface, a health care surface, medical or surgical device, a hospitality sector surface, an industrial sector surface, architectural surfaces, dishware, hard surface packaging, or a combination thereof.

20. The method of claim 18, wherein the contacting step includes the spraying of the peroxycarboxylic acid composition over the solid active oxygen coordinating compound and the peroxycarboxylic acid composition has a contact time of from a few seconds to about 30 minutes, and wherein the peroxycarboxylic acid composition is present in an amount effective for reducing a population of a microorganism selected from the group consisting of spores, bacteria, mold, yeast, viruses and mixtures thereof.

* * * * *